US009251273B2

(12) United States Patent
O'Sullivan et al.

(10) Patent No.: US 9,251,273 B2
(45) Date of Patent: Feb. 2, 2016

(54) DELIVERING A FILTERED SEARCH RESULT

(71) Applicant: International Business Machines Corporation, Armonk, NY (US)

(72) Inventors: Patrick J. O'Sullivan, Dublin (IE); Jeffrey B. Sloyer, Cary, NC (US); Edith H. Stern, Yorktown Heights, NY (US); Barry E. Willner, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 149 days.

(21) Appl. No.: 13/795,630

(22) Filed: Mar. 12, 2013

(65) Prior Publication Data

US 2014/0280038 A1    Sep. 18, 2014

(51) Int. Cl.
*G06F 7/00* (2006.01)
*G06F 17/30* (2006.01)
*C12N 15/82* (2006.01)

(52) U.S. Cl.
CPC ...... *G06F 17/30867* (2013.01); *C12N 15/8286* (2013.01)

(58) Field of Classification Search
CPC ............... G06F 17/30867; G06F 17/30699; G06F 17/30864; G06F 7/24; G06F 17/30091
USPC ........................................................ 707/754
See application file for complete search history.

(56) References Cited

U.S. PATENT DOCUMENTS

| 8,244,721 | B2 | 8/2012 | Morris et al. | |
| 2009/0164929 | A1 * | 6/2009 | Chen et al. | 715/769 |
| 2011/0231383 | A1 | 9/2011 | Smyth | |
| 2012/0278740 | A1 | 11/2012 | Robinson et al. | |
| 2014/0082069 | A1 * | 3/2014 | Varoglu et al. | 709/204 |

\* cited by examiner

*Primary Examiner* — Truong Vo
(74) *Attorney, Agent, or Firm* — Steven L. Nichols; Fabian VanCott

(57) ABSTRACT

Delivering a filtered search result includes identifying a filtered search result in response to a search query from a user that is associated with at least one member of an augmented social group where the augmented social group including social network connections of the user and individuals other than the social network connections who share a common interest with the user and delivering the filtered search result to the user through a user interface.

13 Claims, 4 Drawing Sheets

DELIVERING A FILTERED SEARCH RESULT

BACKGROUND

The present invention relates to delivering a filtered search result to a user, and more specifically, delivering a filtered search result to a user associated with members of the user's augmented social group.

Search engines allow users to input search queries based on keywords. The search engine searches online resources that match the keywords in the search query. The search results are delivered to the user as a listing of results. The results generally include a list of items. Often, the titles of the item, a link to the item's online location, and a short description showing the item's relevance to the keywords are displayed with the items. Some search engines select items to be included in the list based on the item's content and metadata tags. A hyperlink markup language (HTML) title tag of the items can be used as the title of the items in the list while the description tag is used for the short description.

BRIEF SUMMARY

A method of delivering a filtered search result includes identifying a filtered search result in response to a search query from a user that is associated with at least one member of an augmented social group where the augmented social group includes social network connections of the user and individuals other than the social network connections who share a common interest with the user and delivering the filtered search result to the user through a user interface.

A system of delivering a filtered search result includes an augmented social group determination engine to determine members of an augmented social group that includes social network connections of the user and individuals other than the social network connections who share a common interest with the user, an identifying engine to identify a filtered search result in response to the search query from the user that is associated with at least one of the members of the augmented social group, and a delivering engine to deliver the filtered search result to the user through a user interface.

A computer program product for delivering a filtered search result includes a tangible computer readable storage medium, the tangible computer readable storage medium having computer readable program code embodied therewith, the computer readable program code having program instructions that, when executed, cause a processor to determine an interest of a user with identifying keywords in an aggregated data history of the user in textual communications, browsing history, and searching history; determine members of an augmented social group that includes social network connections of the user and individuals other than the social network connections who share a common interest with the user; identify a filtered search result in response to the search query from the user that is linked to at least one of the member of the augmented social group; and deliver the filtered search result to the user through a user interface.

DETAILED DESCRIPTION

Figure 1:
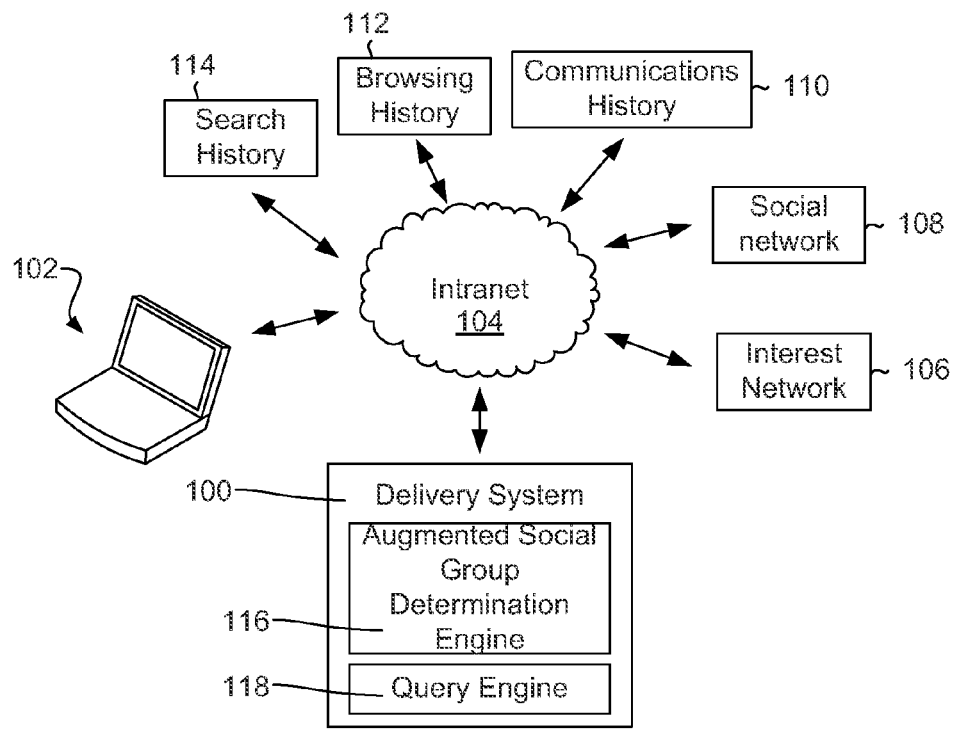
FIG. 1 is a diagram of an example of a delivery system according to one example of the principles described herein.

The present specification describes a method and system for delivering a filtered search result to a user based on the search result's association with a member of the user's augmented social group.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Often, search results delivered to the user include a large amount of information. The large amounts of information can bury the search results of greatest interest to the user. This causes the user to spend a significant amount of time going through the search results to find the results that are the most interesting to the user. Additionally, due to the large volume of data, a user may overlook the search results most interesting to the user.

The principles described herein can cause a reduction in the amount of results returned to the user or prioritize the results in manner that aids the user in finding information of interest to the user. The principles described herein include a method for delivering a filtered search result. Such a method can include identifying a filtered search result in response to a search query from a user that is associated with at least one member of an augmented social group where the augmented social group includes social network connections of the user and individuals other than the social network connections who share a common interest with the user and delivering the filtered search result to the user through a user interface.

Referring now to the figures, FIG. 1 is a diagram of an example of a delivery system (100). In this example, the delivery system (100) is in communication with a client device (102) through an intranet (104). The intranet (104) is also in communication with a user's interest network (106), the user's social network (108), the user's communications history (110), the user's browsing history (112), and the user's search history (114). Further, the delivery system (100) includes an augmented social group determination engine (116) and a query engine (118).

The client device (102) may be any appropriate device that allows the user to access information from the internet. For example, the client device (102) may be a desktop, a laptop, a personal computer, a mobile device, a phone, an electronic tablet, another type of client device, or combinations thereof.

The user may access the delivery system (100) through the client device (102) over the intranet (104). The intranet (104) may be a business intranet, an organization's intranet, another type of intranet, or combinations thereof. While this example is described with reference to intranets, any appropriate type of network may be used in accordance to the principles described herein, such as the internet, local area networks, wide area networks, private virtual networks, other types of networks, or combinations thereof.

The user may input a search query into the query engine (118) of the delivery system (100) through the client device (102). The delivery system (100) may search the resources available in the intranet (104) to find matches to the search query. In response to generating a list of search results, the delivery system (100) filters the search results to provide the user with a more meaningful list of search results. To filter the search results, the delivery system (100) uses an augmented social group determination engine (116) to determine an augmented social group of the user. The delivery system (100) filters the search results based on those items in the search results that are associated with at least one member of the user's augmented social group.

The augmented social group includes the user's social network (108) and the user's interest network (106). The user's social network (108) can be determined by including the user's social networking site connections, email contacts, instant messaging contacts, phone contacts, social networking connections' connections, other forms of contacts or connections, or combinations thereof.

The interest network (106) is made up of individuals that are not already part of the user's social network (108), but share a common interest with the user. The user's interests can be determined by searching the user's aggregated data history. The aggregated data history may include the user's search history (114), the user's browsing history (112), the user's communication history (110), other history pertaining to the user, or combinations thereof. The augmented social group determination engine (116) may find keywords in the user's aggregated data history. For example, the augmented social group determination engine (116) may discover that the user used the keyword "Java" in her communications with others at least seven times within the last week. Such a keyword frequency suggests to the augmented social group determination engine (116) that the user has an interest in Java. The augmented social group determination engine (116) may also search for keywords in the search history (114) and the browsing history (112). The user may control the keyword frequency threshold for determining which keywords constituent an interest.

In some examples, the user's interest for the purpose of determining the user's interest group is constrained to interests relevant to the search. For example, the user may have an interest in Java based on recent communications, but if the search query is on long term evolution (LTE), then the interests used to determine the interest group are constrained to interests that are related to communications. Thus, in such a search query, the interest of Java would not be used to determine the augmented social group. The augmented social group determination system (116) may include mechanisms for determining which of the user's interests will apply to specific search queries based on the user's interests and the terms in the search queries.

The augmented social group determination engine (116) can track the interests of all of its users on a real time basis. Accordingly, the augmented social group determination engine (116) can continuously update interest networks for each of its users.

The user's interests may also be determined by analyzing personal information about a user. For example, the user's social networking site profile may include an interests section that can be used to determine the user's interests. Further, the user's employment title, geographical residence, hobbies, recent trips, other data in the social networking site, or combinations thereof may be used to determine interests of the user.

The augmented social group determination engine (116) may have a constraining factor that limits the size of the interest network (106). For example, the constraining factor may limit the interest network to co-workers, organization membership, profession, industry membership, geographical residence, other restrictions, or combinations thereof. For example, the delivery system (100) may be implemented by a corporation and may purposely limit the delivery system's users to just its employees. As a result, the augmented social group determination engine (116) has a constraining factor that limits the members of the interest group to be the user's co-workers. In other examples, the delivery system (100) is part of a publicly accessible online service and the augmented social group determination engine (116) puts constraining factors on the interest networks (106) to keep the interest networks to a reasonable size. For example, the augmented social group determination engine (116) may limit the interest group to a geographical region without input from the user. In yet other examples, the augmented social group determination engine (116) selects constraining factors based on user input. Further, the augmented social group determination engine (116) may consider multiple factors in a constraining policy to determine how to constrain the size of the interest network.

The augmented social group determination engine (116) may also constrain the size of the interest network based on a time constraint. For example, the keyword frequency may be based on a recent time period, such as a week. In such an example, the user's interest network may change frequently depending on the projects that the user is involved with from week to week. In other examples, the time period is set for months or longer, which causes the interest network to be more consistent over time.

The delivery system (100) uses the augmented social group members to filter the search results. For example, the delivery system (100) determines which of the search results is associated with one of the members of the user's augmented social group. A search result may be associated with a member of the augmented social network if the search result was authored by the member, posted by the member, referenced by the member, rated by the member, contributed to by the member, other associations, or combinations thereof. In some examples, the search result may be associated with the augmented social network member if the search result mentions the member.

The delivery system (100) may deliver just those search results that are associated with the members of the augmented social group. In other examples, the delivery system (100) prioritizes the search results that are associated with the members of the social network before listing the other search results. The order of the filtered search results may be based on an ordering policy. The ordering policy may include rules and factors that account for whether the member is from the social network, whether the member is from the interest network, the strength of the user's interest, the strength of the member's interest, the number of interests that the user and the member have in common, relevancy to the search query, other factors, or combinations thereof.

Figure 2:
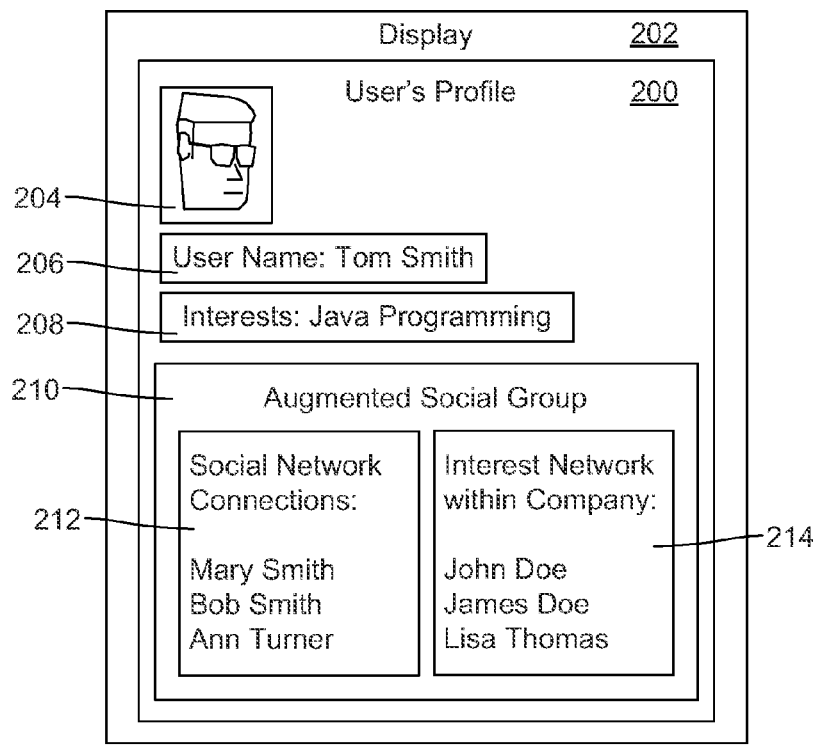
FIG. 2 is a diagram of an example of a user's profile according to one example of the principles described herein.

FIG. 2 is a diagram of an example of a user's profile (200) according to one example of the principles described herein. In this example, the user's profile (200) is part of a company intranet and is displayed in a display (202) of a client device. The user's profile (200) includes an image (204), the user's name (206), a list (208) of interests, and the user's augmented social group (210).

The augmented social group (210) includes the user's social network connections (212) and the members of the user's interest network (214) within the company. Other members of the user's social network connections may include email contacts, instant messaging contacts, contacts stored in the user's phone, other contacts, or combinations thereof. The members of the interest network (214) are not the user's social network connections (212). The interests may be determined from information in the user's profile, from the user's communications, from the user's browsing history, from the user's search history, from other areas of the user's aggregated data history, or combinations thereof.

While the examples above have been described with reference to specific mechanisms for determining members of the user's interest network, any appropriate mechanisms for determining members of the user's interest network may be used in accordance with the principles described herein. Further, while the examples above have been described with reference to specific mechanisms for determining the user's social network connections, any appropriate mechanisms for determining the user's social networking connections may be used.

Figure 3:
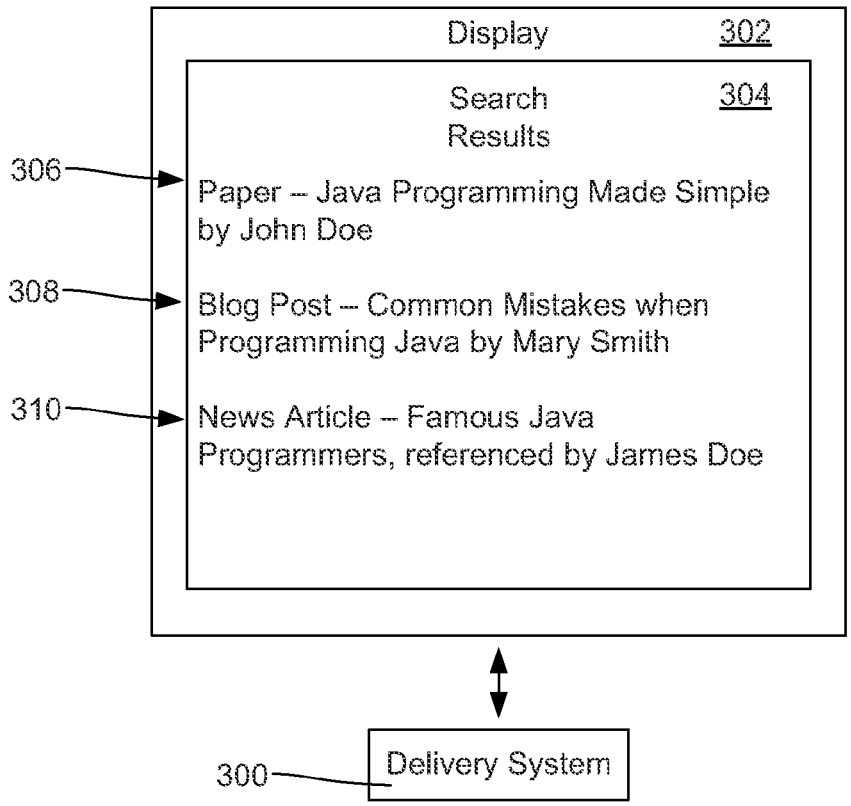
FIG. 3 is a diagram of an example of delivering filtered search results according to one example of the principles described herein.

FIG. 3 is a diagram of an example of delivering filtered search results, in this example, the delivery system (300) is in communication with a display (302). The display includes filtered search results (304).

The user inputs a search query into the delivery system (300). The delivery system (300) searches for items that match the terms in the search query. In response to finding search results, the delivery system (300) analyzes the search results to determine whether any of the search results is associated with any of the members of the user's augmented social group. If so, the delivery system (300) delivers the search results associated with the members of the augmented social group.

In this example, the delivery system (300) delivers just those search results that are associated with the members of the augmented social group. For example, a paper (306) written by John Doe, a member of the user's interest network (214, FIG. 2), is listed in the filtered search results. Further, a blog post (308) posted by Mary Smith, one of the user's social network connections (212, FIG. 2), is also listed in the filtered search results. Additionally, a news article (310) referenced by James Doe, another member of the user's interest network (214, FIG. 2), is listed in the filtered search results. Each of the search results is somehow associated with a member of the augmented social group through authorship, posting, referencing, another type of association, or combinations thereof. In this example, just those search results that are associated with a member of the augmented social group are included in the filtered search results. In other examples, the search results that are associated with the augmented social group are included in a more inclusive list of search results, but those search results that are associated with a member of the augmented social group are prioritized in the search results' listing to assist the user in finding the search results that are likely to be of more interest.

The order that the search results associated with members of the augmented social group are listed in the filtered search results may be determined by an ordering policy. The ordering policy may consider factors based on how many members of the augmented social group are associated with the search results, whether a member of an interest network is associated with the search results, whether a social network connection is associated with the search result, the keyword relevancy of the search result, the strength of the user's interest with the interest network member, other factors, or combinations thereof.

The user may input a search query into a search field provided by the delivery system (300) that is related to a project that the user is working on for her employer. The filtered search results helps the user find relevant material from either those that the user is already working with (those in the user's social network) or from those who have common interests with the user. Within the user's company, it is likely that there are some people with whom the user has never worked with, but who have information that is relevant to the user's job. For example, the user may be involved in developing Java products for her employer. While the user is involved with development, the user may not be directly involved with those that market Java products in the company. However, the marketers working with Java products are likely to be in the user's interest network. Thus, the filtered search results are likely to find search results from those marketers.

While this example has been described with reference to specific ways of delivering and/or ordering the filtered search results to the user, any appropriate mechanisms for delivering and/or ordering the filtered search results may be used in accordance with the principles described herein. Further, while the examples above have been described with reference to specific mechanisms for determining a user's interest, any appropriate mechanism for determining a user's interest may be used in accordance with the principles described herein.

Figure 4:
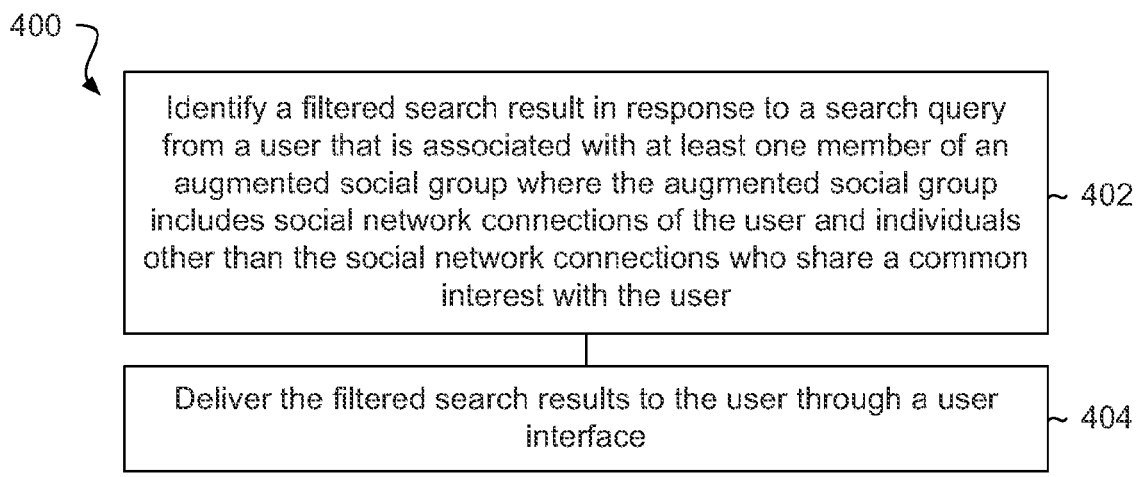
FIG. 4 is a diagram of an example of a method for delivering a filtered search result according to one example of the principles described herein.

FIG. 4 is a diagram of an example of a method (400) for delivering a filtered search result. In this example, the method (400) includes identifying (402) a filtered search result in response to a search query from a user that is associated with at least one member of an augmented social group where the augmented social group includes social network connections of the user and individuals other than the social network connections who share a common interest with the user and delivering (404) the filtered search results to the user through a user interface.

The method may also include determining the membership of the augmented social network. The social network connections may include social networking site connections, email contacts, instant messaging contacts, phone contacts, other types of contacts or connections, or combinations thereof.

The common interests of the user may be determined by analyzing the user's aggregated data history, which may include the user's browsing history, search history, and communications history. For example, the delivery system may look for keywords in the user's communications (emits, instant messages, etc), search queries, in the uniform resource locations (URLs) of the websites visited by the user, other histories, or combinations thereof. Further, the aggregated data history may include the content in the user's social networking site, such as listed interests, job title, office location, other social profile information, or combinations thereof.

The size of the interest network, and therefore the size of the augmented social network, may be limited by a constraining factor. For example, a constraining factor may be constrained by a geographic location, a time period, a membership in an organization, employment in a company, other constraining factors, or combinations thereof. The social network connections include the connections of those that the user is directly connected to. For example, if a search result matches the content of the search query and the search result is associated with a connection of one of the user's connections, the search result will be included in the filtered search results.

The delivering system may deliver just those search results that are associated with members of the augmented social group. In other examples, the filtered search results include more than just those results that are associated with the members of the augmented social group, but the search results that are associated with the members of the augmented social group are displayed in such a way to catch the user's attention. For example, the results associated with members of the augmented social group may be prioritized to the front of the listed results. In other examples, the results associated with members of the augmented social group are highlighted, bolded, underlined, italicized, indented, or otherwise marked to catch the user's attention.

Figure 5:
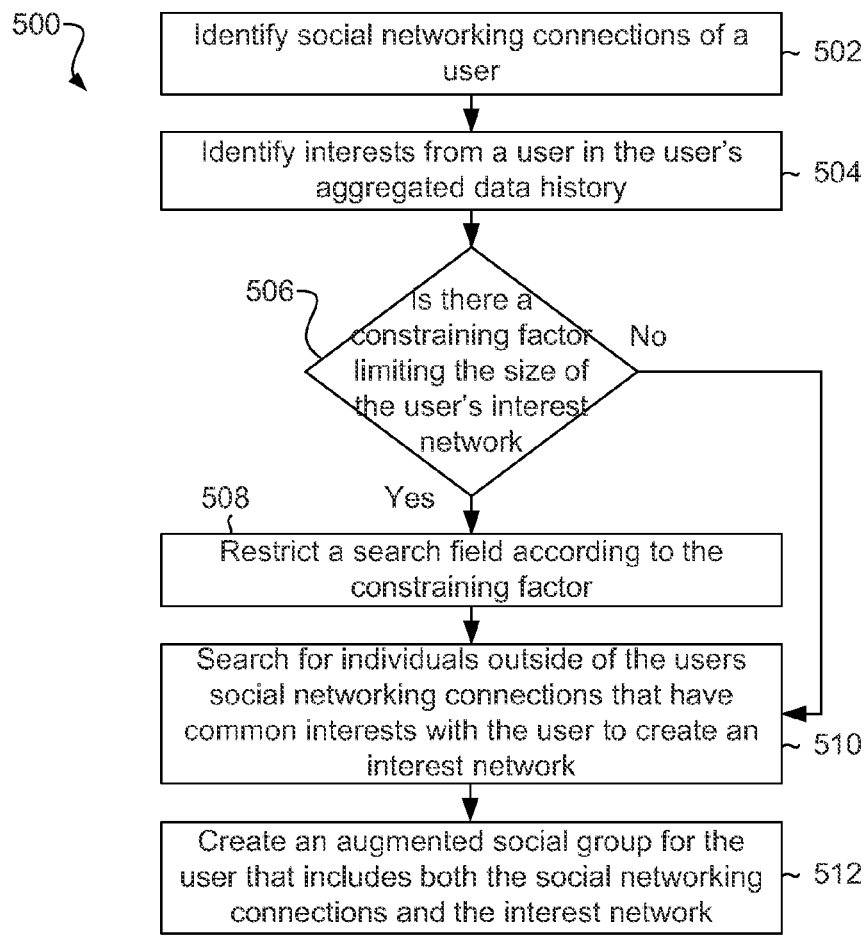
FIG. 5 is a diagram of an example of a method for creating an augmented social group according to one example of the principles described herein.

FIG. 5 is a diagram of an example of a method (500) for creating an augmented social group. In this example, the method (500) includes identifying (502) social networking connections of a user, and identifying (504) interests from a user's aggregated data history. The method also includes determining (506) whether there is a constraining factor restricting the size of the user's interest network. If there is a constraining factor, the method includes restricting (508) a search field for the interest network according to the constraining factor. The method continues with searching (510) for individuals outside of the user's social networking connections that have common interests with the user to create an interest network, and creating (512) an augmented social group for the user that includes both the social networking connections and the interest network.

Figure 6:
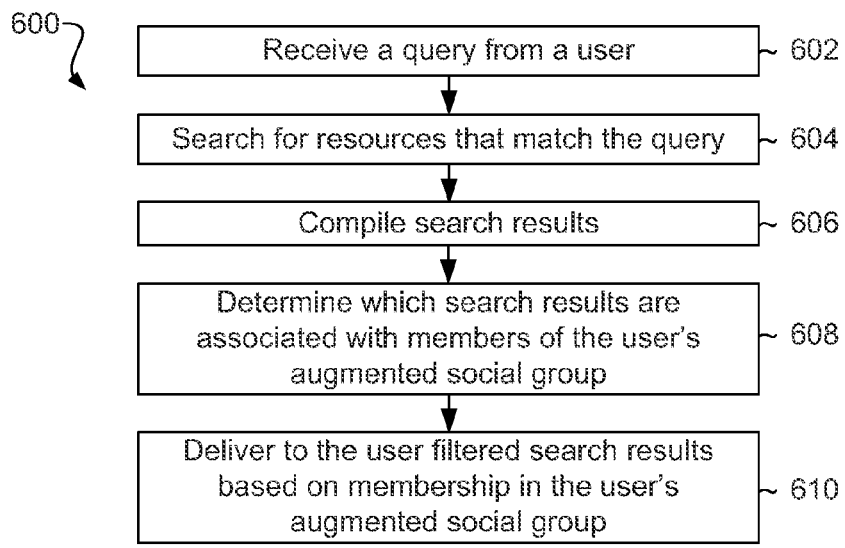
FIG. 6 is a diagram of an example of a method for delivering a filtered search result according to one example of the principles described herein.

FIG. 6 is a diagram of an example of a method (600) for delivering a filtered search result. In this example, the method (600) includes receiving (602) a query from a user, searching (604) for resources that match the query, and compiling (606) the search results. The method (600) also includes determining (608) which search results are associated with members of the user's augmented social group, and delivering (610) to the user filtered search results based on membership in the user's augmented social group.

In other examples, the search may be restricted to search just materials that are associated with the members of the augmented social network. In such examples, the search is filtered, so fewer results are retrieved overall. However, the results from the filtered search are more relevant than if the search was unrestricted. Further, in such an example, the search results may not be filtered after the search because the results are already filtered since the search was restricted to just materials associated with the members of the augmented social network.

Figure 7:
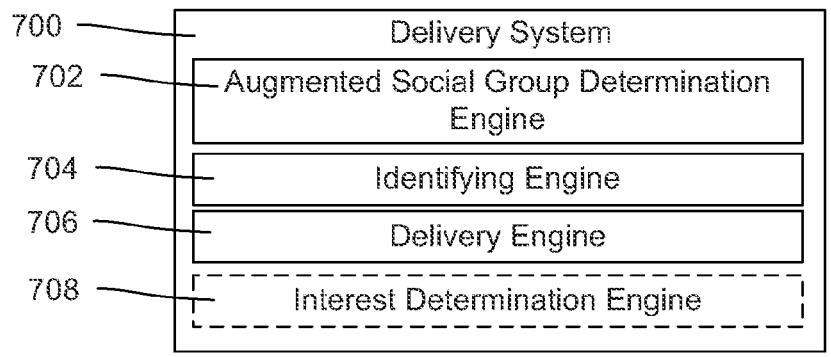
FIG. 7 is a diagram of an example of a delivery system according to one example of the principles described herein.

FIG. 7 is a diagram of an example of a delivery system (700) according to one example of the principles described herein. The delivery system (700) includes an augmented social group determination engine (702) an identifying engine (704) and a delivery engine (706). In this example, the delivery system (700) also includes an interest determination engine (708). The engines (702, 704, 706, 708) refer to a combination of hardware and program instructions to perform a designated function. Each of the engines (702, 704, 706, 708) may include a processor and memory. The program instructions are stored in the memory and cause the processor to execute the designated function of the engine.

The augmented social group determination engine (702) determines the members of the augmented social group from both the user's interest network and social network. In some examples, the augmented social group determination engine (702) uses the interest determination engine (708) to determine the interests of the user to construct the user's interest network. The identifying engine (704) identifies a filtered search result that is associated with at least one member of the augmented social group. The delivery engine (706) delivers the filtered search result to the user through a display of a client device.

Figure 8:
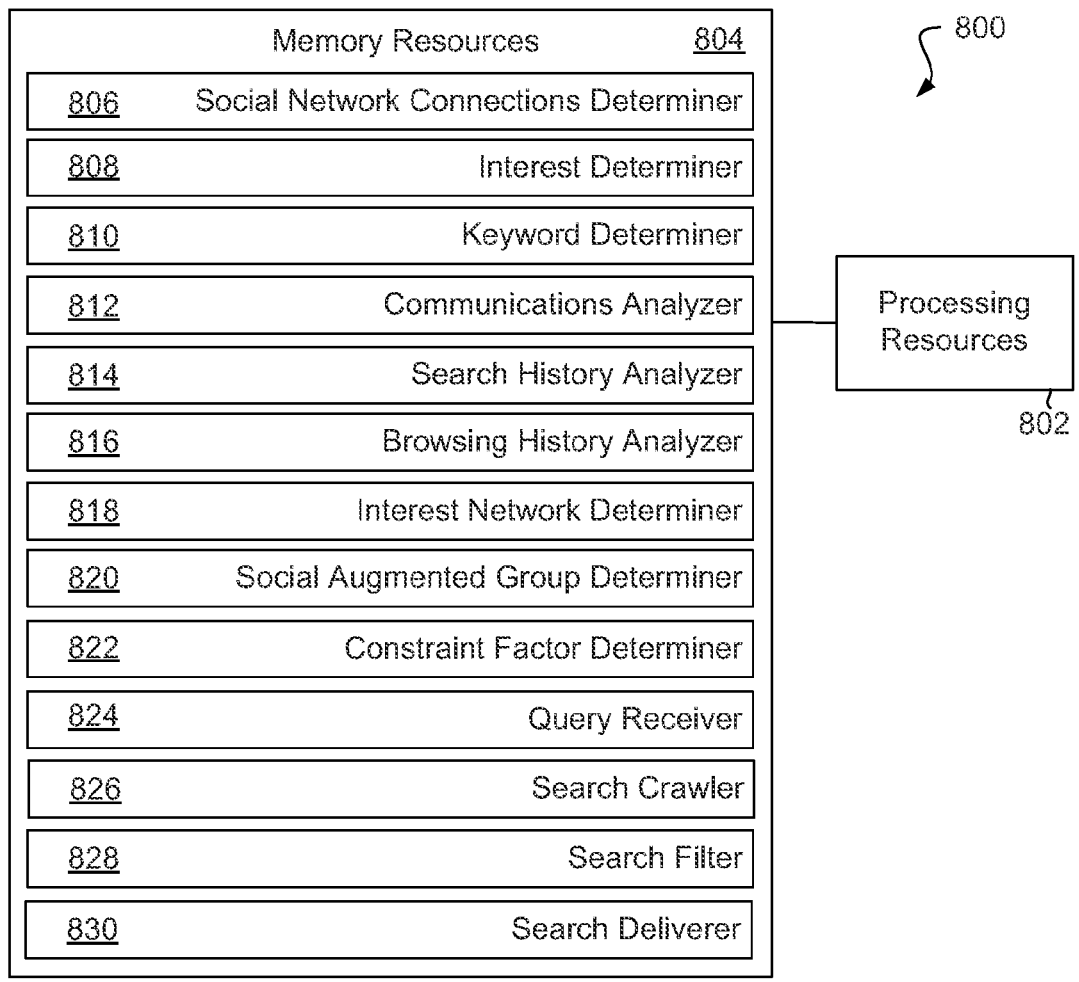
FIG. 8 is a diagram of another example of a delivery system according to one example of the principles described herein.

FIG. 8 is a diagram of another example of a delivery system. In this example, the delivery system (800) includes processing resources (802) that are in communication with memory resources (804). Processing resources (802) include at least one processor and other resources used to process programmed instructions. The memory resources (804) represent generally any memory capable of storing data such as programmed instructions or data structures used by the delivery system (800). The programmed instructions shown stored in the memory resources (804) include a social network connections determiner (806), an interest determiner (808), a keyword determiner (810), a communications analyzer (812), a search history analyzer (814), a browsing history analyzer (816), an interest network determiner (818), asocial augmented group determiner (820), a constraint factor determiner (822), a query receiver (824), a search crawler (826), a search filter (828), and a search deliverer (830).

The memory resources (804) include a computer readable storage medium that contains computer readable program code to cause tasks to be executed by the processing resources (802). The computer readable storage medium is a tangible storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic storage media, or types of memory, or combinations thereof.

The social network connections determiner (806) represents programmed instructions that, when executed, cause the processing resources (802) to determine the social network connections of a user. The social network connections may be connections from a social networking site, email contacts, instant messaging contacts, phone contacts, or other types of contacts, or combinations thereof.

The interest determiner (808) represents programmed instructions that, when executed, cause the processing resources (802) to determine the interests of the user. The keyword determiner (810) represents programmed instructions that, when executed, cause the processing resources (802) to determine the keywords in the user's aggregated data history. The identified keywords are relayed by the keyword determiner (810) to the interest determiner (808) as input. The communications analyzer (812) represents programmed instructions that, when executed, cause the processing, resources (802) to analyze textual communications to or from the user. The communications analyzer (812) works with the keyword determiner (810) to identify keywords in the user's communications. The search history analyzer (814) represents programmed instructions that, when executed, cause the processing resources (802) to analyze the searches performed by the user. The search history analyzer (814) works with the keyword determiner (810) to identify keywords in the user's search history. The browsing history analyzer (816) represents programmed instructions that, when executed, cause the processing resources (802) to analyze the online locations that the user has visited through a browser. The browsing history analyzer (816) works with the keyword determiner (810) to identify keywords in the user's browsing history. The interest network determiner (818) represents programmed instructions that, when executed, cause the processing resources (802) to determine individuals who are not already in the user's social connections, but who share a common interest. Such individuals are classified as being members of the user's interest network.

The social augmented group determiner (820) represents programmed instructions that, when executed, cause the processing resources (802) to determine the user's augmented social group, which combines the members of the user's social network and the user's interest network. A constraint factor determiner (822) represents programmed instructions that, when executed, cause the processing resources (802) to determine the constraint factors that control the size of the user's augmented social network. For example, the constraint factor determiner (822) may determine a rule that the members of the user's interest group can be just those who are employed by the user's employer. In other examples, the constraining factor determiner (822) may include a rule that indicates that the user's interests should be constrained to the interests expressed through the user's aggregated data history within a recent time period. In yet other examples, the constraining factor determiner (82) may also indicate that just the social connections directly connected to the user are to be included in the user's social network versus including the user's connections and those connected to the user's connections. The constraint factor determiner (822) may determine the appropriate constraints based on the information relevant to the search. For example, on a confidential matter having to do with strategy, the constraint may constrain the members of the social augmented network to be just those within the user's company. For non-confidential matters, the constraint may be less restrictive, such as constraining the augmented social group members to be individuals within the user's company and the company's business partners.

The query receiver (824) represents programmed instructions that, when executed, cause the processing resources (802) to receive a search query from the user. The search crawler (826) represents programmed instructions that, when executed, cause the processing resources (802) to crawl online resources to identify search results that match the terms in the user's search query. The search fitter (828) represents programmed instructions that, when executed, cause the processing resources (802) to filter the search results to identify those search results that are associated with members of the user's augmented social network. The search deliverer (830) represents programmed instructions that, when executed, cause the processing resources (802) to deliver the filtered search results to the user. In some examples, the search deliverer (830) delivers just the filtered search results that are associated with members of the user's augmented social group. In other examples, the filtered search results include both search results that are associated with members of the user's augmented social group and search results that are not. However, the search results that are associated with members of the user's augmented social group are prioritized over those search results that are not.

Further, the memory resources (80.4) may be part of an installation package. In response to installing the installation package, the programmed instructions of the memory resources (804) may be downloaded from the installation package's source, such as a portable medium, a server, a remote network location, another location, or combinations thereof. Portable memory media that are compatible with the principles described herein include DVDs, CDs, flash memory, portable disks, magnetic disks; optical disks, other forms of portable memory, or combinations thereof. In other examples, the program instructions are already installed. Here, the memory resources can include integrated memory such as a hard drive, a solid state hard drive, or the like.

In some examples, the processing resources (802) and the memory resources (804) are located within the same physical component, such as a server, or a network component. The memory resources (804) may be part of the physical component's main memory, caches, registers, non-volatile memory, or elsewhere in the physical component's memory hierarchy. Alternatively, the memory resources (804) may be in communication with the processing resources (802) over a network. Further, the data structures, such as the libraries and may be accessed from a remote location over a network connection white the programmed instructions are located locally. Thus, the delivery system (800) may be implemented on a user device, on a server, on a collection of servers, or combinations thereof.

The delivery system (800) of FIG. 8 may be part of a general purpose computer. However, in alternative examples, the delivery system (800) is part of an application specific integrated circuit.

While the examples above have been described with reference to specific associations with the search results and the members of the augmented social group, the search results may be associated in any appropriate manner with the members of the augmented social group in accordance with the principles described herein. Further, while the examples above have been described with reference to specific mechanisms for searching for search results, any appropriate mechanism for searching for search results may be used in accordance with the principles described herein. Also, while the examples above have been described with reference to specific constraining factors to constrain the size of the user's augmented social group, any appropriate constraining factor may be used to constrain the size of the user's augmented social group.

The descriptions of the various examples of the present invention have been presented for purposes of illustration, but are not intended to be exhaustive or limited to the examples disclosed. Many modifications and variations will be apparent to those of ordinary skill in the art without departing from the scope and spirit of the described examples. For example, the sequence of tasks performed in a method may be performed in an appropriate manner that brings about the intended purpose of such a method. The terminology used herein was chosen to best explain the principles of the examples, the practical application or technical improvement over technologies found in the marketplace, or to enable others of ordinary skill in the art to understand the examples disclosed herein.

What is claimed is:

1. A method for delivering a filtered search result, comprising:
    determining at least one interest of a user, with identifying keywords, from an aggregated data history of said user, the aggregated data history of the user comprising all of the user's textual communications, browsing history, and searching history;
    determining members of an augmented social group that includes social network connections of said user, comprising all of social networking site connections, email contacts and phone contacts of said user;
    adding to said augment social group a number of additional individuals, other than said social network connections of said user, the number of additional individuals being individuals who share at least one of the interests of the user as determined from the aggregated data history of the user, wherein the number of individuals sharing at least one of the interests of said user are identified using the keywords identifying a corresponding interest of the user;
    filtering a search result in response to a search query from a user to exclude some entries in the search result, wherein the filtering is based on items in the search result that are associated with at least one member of the augmented social group; and
    delivering said filtered search result to said user through a user interface.

2. The method of claim 1, wherein delivering said filtered search result to said user includes prioritizing said filtered search result in an inclusive list.

3. The method of claim 1, wherein said augmented social group is constrained with a constraining factor that restricts a size of a group of said individuals other than said social network connections who share a common interest with said user.

4. The method of claim 3, wherein said constraining factor is selected from a group consisting of co-workers, organization membership, profession, industry membership, and geographical residence.

5. The method of claim 3, wherein said constraining factor is a time period wherein said common interests are constrained to interests of said user within said time period.

6. The method of claim 1, wherein determining said common interest with said individuals from said aggregated data history of said user includes identifying keywords in textual communications from said user.

7. The method of claim 1, wherein determining said common interest with said individuals from said aggregated data history of said user includes information included in social networking profiles.

8. The method of claim 1, wherein filtering said search result based on items associated with at least one member of the augment social group comprises identifying a searchable content that is authored by said at least one member, posted by said at least one member, or referenced by said at least one member.

9. A system for delivering a filtered search result, comprising processing and memory resources, the system comprising, implemented with the processing and memory resources:
    an interest determiner for determining at least one interest of a user from an aggregated data history of said user, the aggregated data history of the user comprising all of said user's textual communications, browsing history, and searching history;
a keyword determiner for determining at least one keyword associated with each interest of said user determined by said interest determiner;
a social network connections determiner for determining a group of social network connections of said user, the social network connections comprising all of social networking site connections, email contacts and phone contacts of said user;
an interest network determiner for determining a number of additional individuals being individuals who share at least one of the interests of the user identified by the interest determiner from the aggregated data history of the user, wherein the number of individuals sharing at least one of the interests of said user are identified using the keywords identified by the keyword determiner including use of a said keyword in a textual communication between said user and one of said additional individuals;
an augmented social group determination engine to determine members of an augmented social group that includes said social network connections of a user identified by the social network connections determiner and said additional individuals, other than said social network connections, who share a common interest with said user as determined by the interest network determiner;
an identifying engine to identify a filtered search result in response to a search query from said user that is associated with at least one of said members of said augmented social group; and
a delivering engine to deliver said filtered search result to said user through a user interface;
wherein said augmented social group is constrained with a constraining factor that restricts a number of said individuals other than said social network connections that are included in said augmented social group.

10. The system of claim 9, wherein the augmented social group determination engine is constrained to using common interests that are relevant to the search query when determining which individuals other than said social network connections are included in said augmented social group.

11. A computer program product for delivering a filtered search result, comprising:
a non-transitory tangible computer readable storage medium, said tangible computer readable storage medium comprising computer readable program code embodied therewith, said computer readable program code comprising program instructions that, when executed, causes a processor to:
determine an interest of a user with identifying keywords in an aggregated data history of said user in textual communications, browsing history, and searching history;
determine members of an augmented social group that includes social network connections of said user, comprising all of social networking site connections, email contacts and phone contacts, and individuals other than said social network connections who share a common interest with said user as determined by keywords used in communications made by the user to other individuals;
filter items in a search result generated in response to a search query from said user, wherein filtering is based on which items in the search result are associated with at least one of said members of said augmented social group; and
deliver said filtered search result to said user through a user interface.

12. The computer program product of claim 11, further comprising computer readable program code comprising program instructions that, when executed, causes said processor to prioritize said filtered search result in an inclusive list.

13. The computer program product of claim 11, further comprising computer readable program code comprising program instructions that, when executed, causes said processor to include in said filtered search result content that is authored by or posted by at least one of said members of said augmented social group.

* * * * *